United States Patent [19]
Bock

[11] Patent Number: 5,618,275
[45] Date of Patent: Apr. 8, 1997

[54] ULTRASONIC METHOD AND APPARATUS FOR COSMETIC AND DERMATOLOGICAL APPLICATIONS

[75] Inventor: Robert T. Bock, Brewster, N.Y.

[73] Assignee: Sonex International Corporation, Brewster, N.Y.

[21] Appl. No.: 549,488

[22] Filed: Oct. 27, 1995

[51] Int. Cl.⁶ .......................... A61M 35/00; A61B 17/20
[52] U.S. Cl. ................. 604/290; 601/2; 604/20; 604/22; 604/890.1
[58] Field of Search .................. 604/19–22, 890.1, 604/289–90, 310, 118, 131; 607/1–3, 61, 72; 601/2; 128/662.03

[56] References Cited

U.S. PATENT DOCUMENTS

| | | |
|---|---|---|
| 4,040,414 | 8/1977 | Suroff . |
| 4,309,989 | 1/1982 | Fahim . |
| 4,535,759 | 8/1985 | Polk ............................................. 601/2 |
| 4,787,888 | 11/1988 | Fox ............................................. 601/2 |
| 4,866,050 | 9/1989 | Ben-Amoz . |
| 5,016,615 | 5/1991 | Driller ....................................... 604/20 |
| 5,111,822 | 5/1992 | Dory ........................................... 601/2 |
| 5,323,769 | 6/1994 | Bommannan ............................ 601/2 |
| 5,415,629 | 5/1995 | Henley . |
| 5,421,816 | 6/1995 | Lipkovker ................................. 604/20 |
| 5,431,664 | 7/1995 | Ureche ....................................... 604/22 |
| 5,503,154 | 4/1996 | Belef ................................. 128/662.03 |

FOREIGN PATENT DOCUMENTS

| | | | |
|---|---|---|---|
| 654254 | 3/1979 | U.S.S.R. ............................... 604/20 |
| 931191 | 5/1982 | U.S.S.R. ............................... 601/2 |
| 9316652 | 9/1993 | WIPO .................................... 601/2 |
| 4005368 | 3/1994 | WIPO .................................... 604/20 |

Primary Examiner—Vincent Millin
Assistant Examiner—Ellen Tao
Attorney, Agent, or Firm—Watson Cole Stevens Davis, P.L.L.C.

[57] ABSTRACT

Low frequency ultrasonic pressure waves of high intensity are applied to the skin to cause cavitation. A therapeutic agent may be applied to the skin in a predetermined amount prior to the application of the pressure waves. The therapeutic agent may also be applied to the skin subsequent to the application of the pressure waves. Ultrasonic pressure waves of high frequency which do not cause cavitation may be applied to the skin after delivery of a therapeutic agent. The depth of penetration of the agent may be controlled by varying the burst width of electrical signals applied to a piezoelectric transducer. A housing surrounds the transducer and a sleeve may be provided to define with the housing a predetermined controlled volume chamber for holding a measured amount of agent. An ultrasonic power supply includes means for generating both low and high ultrasonic frequency electric signals, and a switch alternatively connects the high and low frequency signals to the transducer.

11 Claims, 5 Drawing Sheets

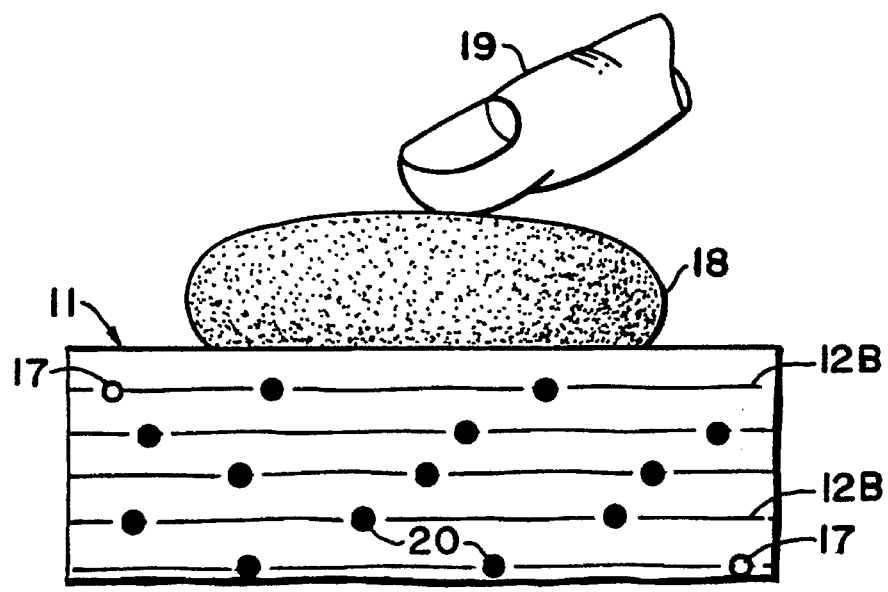
FIG.IC
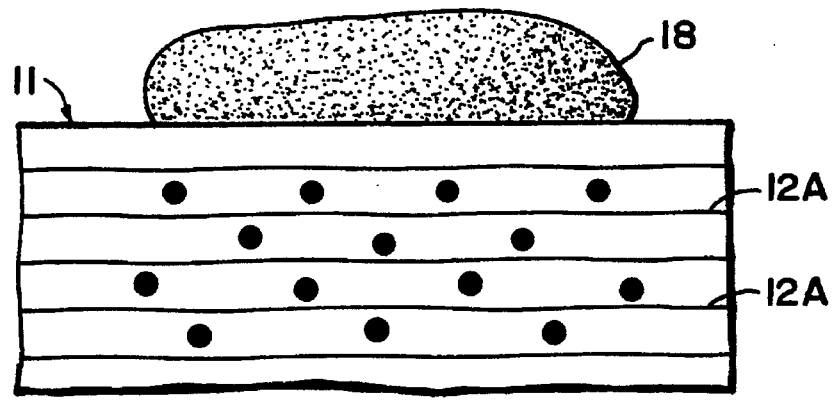
FIG.ID

ULTRASONIC METHOD AND APPARATUS FOR COSMETIC AND DERMATOLOGICAL APPLICATIONS

BACKGROUND OF THE INVENTION

1. Field of the Invention

This invention relates to ultrasonic devices for cosmetic and dermatological applications. More particularly, the invention is concerned with methods and apparatus facilitating the use of ultrasonic energy coupled to anatomical tissue to precondition the skin to allow the penetration of medical and cosmetic compounds, to drive these compounds into and through the epidermis, into the dermis, into the anatomical tissue below the dermis and into the blood supply when required. The invention is particularly effective to control the depth of penetration and the dosage of medications to be delivered to eliminate the harmful side effects associated with some of the systemically delivered medications.

2. Description of Prior Art

Numerous attempts have been made in the past to deliver medications through the skin by chemical, electrical and ultrasonic means. The application of chemicals to modify the skin structure to allow the penetration of drugs was found to be dangerous because while it provided access for drugs to penetrate, it left the body unprotected against harmful environments. The application of electrical fields to create transient transport pathways by a method called electroporation, and the method to electrically charge drug molecules to increase their penetration through the skin called iontophoresis, have both been proven ineffective to deliver therapeutically adequate dosage of medications through the skin. Past applications of high frequency (0.5 to 3 megahertz) and high intensity (0.5 to 5 W/cm$^2$) therapeutic ultrasound, called sonophoresis, were found to be uncertain, inefficient, and the method found limited clinical applications.

The efforts of the prior art of ultrasonically induced drug delivery (sonophoresis) were focused on driving drug molecules through the skin by the applications of high (megahertz) frequency high energy ultrasonic pressure waves. This procedure particularly suffered from the disadvantage of tissue heating and the associated modification and sometimes destruction of healthy cells. Once adequate ultrasonic power is applied either in a continuous wave ultrasonic modality, or maximum burst length that is practicable without adverse tissue heating effects to force drug molecules through the highly resistive outermost sealing layer of the skin, the stratum corneum (SC), the drugs typically will proceed uncontrollably through the less resistive dermis into the blood system, creating systemic absorption of the drugs which is undesirable in most dermatological applications.

What has occurred to date is that notwithstanding the teachings of the prior art, the ability to deliver dermatological drugs topically, safely, effectively, inexpensively, and easily in a home environment has remained unsolved.

Responding to the above described unresolved needs, the object of this invention is to provide a method and apparatus for the pretreatment of the skin to open up passageways through the epidermis and to allow the penetration of medications or cosmetics for a limited time period, in such a method which seals the skin automatically within a short period of time after the topical application of the drugs to restore the environmental protection of the body.

Another object of the invention is to provide a method and apparatus of ultrasound medicated drug delivery where the amount of the drug (dosage) and the depth of the penetration of the drug is controlled.

A further object of the invention is the elimination of paring of warts to provide access for the therapeutic compounds into the deeper structure of the warts, without surgical procedures. This is a particularly important feature when treating AIDS patients.

Yet another object of the invention is to provide a method and apparatus to speedily restore the sealing properties of the skin upon the completion of the ultrasound medicated delivery of the medication and to provide immediate environmental protection of the body. Further objects and advantages will be apparent from the examination of the drawings and the specification.

SUMMARY OF THE INVENTION

In the methods of the invention, low frequency ultrasonic pressure waves are applied to the skin of sufficiently high intensity to cause cavitation in the skin which facilitates penetration of a therapeutic agent such as medicine or a cosmetic such as a moisturizer. In one method of the invention, the therapeutic agent is applied to the skin prior to the application of the ultrasonic pressure waves. In this method, a predetermined controlled amount of a therapeutic agent may be applied to the skin. A novel apparatus is provided with measuring means which accurately measured the amount of agent that is applied.

In another method of the invention, a therapeutic agent is applied to the skin subsequent to application of the ultrasonic pressure waves. In a further method of the invention, ultrasonic pressure waves of high frequency are applied to the skin after the completion of delivery of a therapeutic agent so as not to cause cavitation in the skin, thereby assisting the restoration of the sealing properties of the skin. In a still further method of the invention, the depth of penetration of a therapeutic agent into the skin is controlled by varying the burst width high frequency electrical signals which are applied to the transducer of the invention.

In the above discussion, the term therapeutic agent refers to a single medication or cosmetics or a plurality of medicines or cosmetics and any mixture thereof.

BRIEF DESCRIPTION OF THE DRAWINGS

FIGS. 1A–1D show cross-sectional views of the skin and the invention designed for the pretreatment of the skin to open up passageways through the stratum corneum, in a time-phased sequence. FIG. 1A shows the skin condition before treatment, FIG. 1B shows the energized apparatus preconditioning the skin by developing the passageways in the skin, FIG. 1C shows the apparatus removed and the medication applied into the opened up passageways, FIG. 1D shows the resealed skin condition after treatment;

DESCRIPTION OF THE INVENTION

Figure 1A:
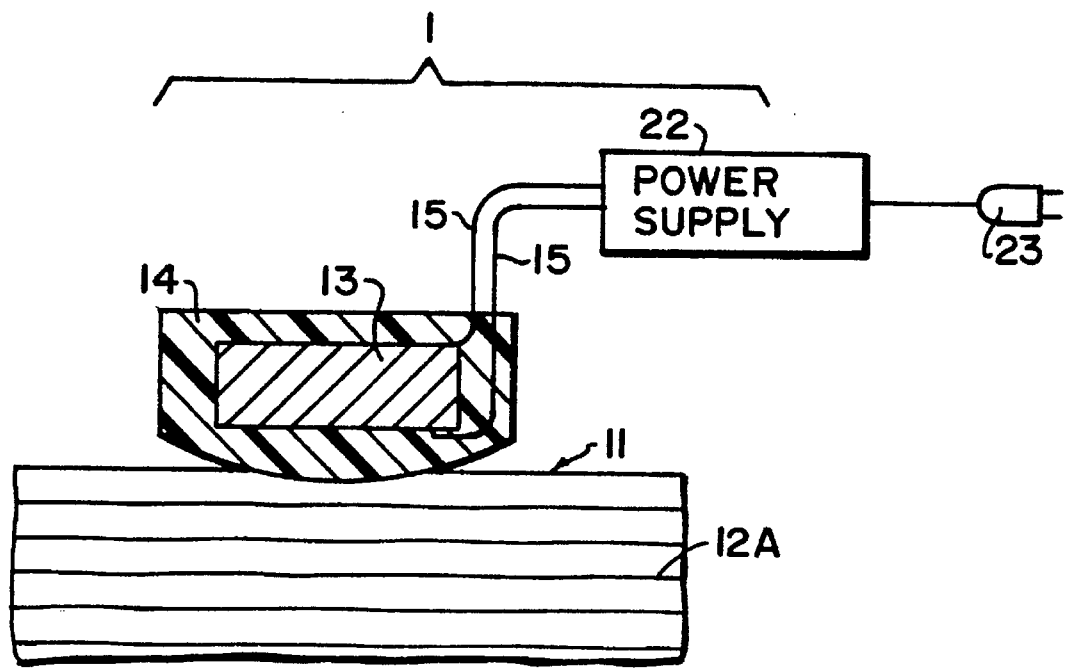

Referring in detail to the drawings, like reference numerals herein refer to similar parts in the drawings. In the following discussion, unless otherwise qualified, the term "ultrasound" refers to either continuous wave ultrasound or a repetitive burst type ultrasonic modality, and refers to both high frequency but still audible sound and high frequency sound waves which are above the sensory capabilities of the human ear.

An ultrasonic skin conditioning device 1, in accordance with the simplest form of the present invention, is shown in FIG. 1A. The skin conditioning device 1 comprises a piezoelectric transducer 13 and connecting wiring 15 that connects the transducer 13 to the external ultrasonic power supply 22. The external power supply draws its power either from a standard household current through a connector 23 or is operated from a battery within the power supply. The piezoelectric transducer 13 is encapsulated in a housing 14 made of a rigid material such as plastic having a smooth curved surface shown in position on top of the outer surface of the stratum corneum 11, the outermost skin layer consisting of flat, dead cells filled with keratin fibers surrounded by ordered lipid bilayers 12A. This ordered structure of the lipid bilayers normally provides an impermeable protection of the anatomy.

Figure 1B:
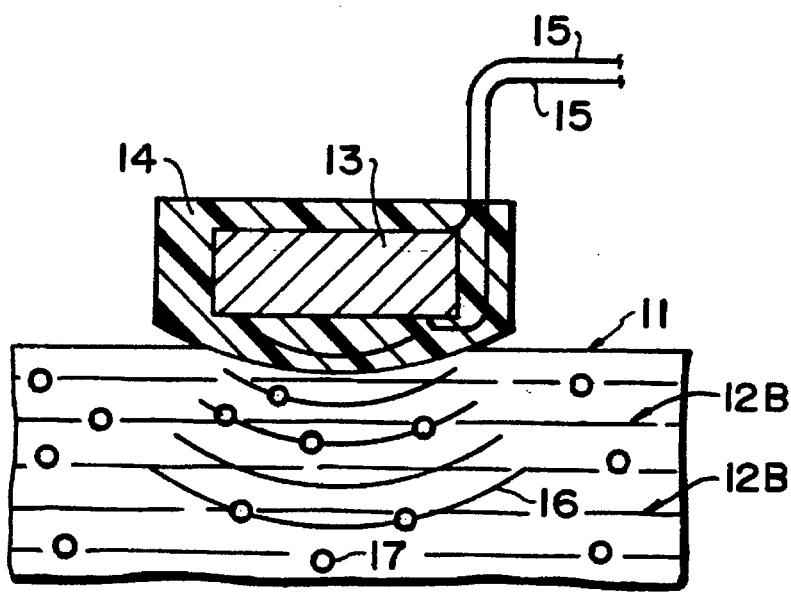

FIG. 1B shows the energized transducer 13 generating ultrasonic waves 16 in the frequency range of 15,000 to 25,000 Hertz, providing ultrasonic cavitation to develop, grow and oscillate microscopic air and/or vacuum pockets 17 which act to disorganize the lipid bilayers 12B depicted by dashed lines in this illustration. The vacuum pockets and the disorganization of the lipid bilayers temporarily eliminate the barrier properties of the skin, and provide penetrable channels for medical and cosmetic compounds through the epidermis into the deeper layers of the living skin and the underlying tissues. These penetrable channels will remain open for a short period of time, providing opportunity for the penetration of a therapeutic agent, until the body's repair function reorganizes the lipid bilayers into an ordered form again, effectively sealing the body.

FIG. 1C depicts the placement of a body of therapeutic agent or compounds 18 onto the outside surface of the skin 11 and the rubbing of the compounds 18 into the skin by the fingers 19 of the user. This must be done promptly before the natural function of the body decreases the permeability of the skin to restore the environmental protection of the body. Finding the open channels through the disordered lipid bilayers 12B, the molecules 20 of the therapeutic compounds will penetrate through the stratum corneum into the living skin and underlying tissues. FIG. 1D shows the reorganized status of the stratum corneum, the lipid bilayers 12A in an ordered structure, sealing the body against further penetration of both desired and undesired invading molecules. The molecules 20 of the therapeutic compounds which did not go through the stratum corneum into the living skin and underlying tissues are sealed in place and will be dissolved slowly by the body.

Figure 2A:
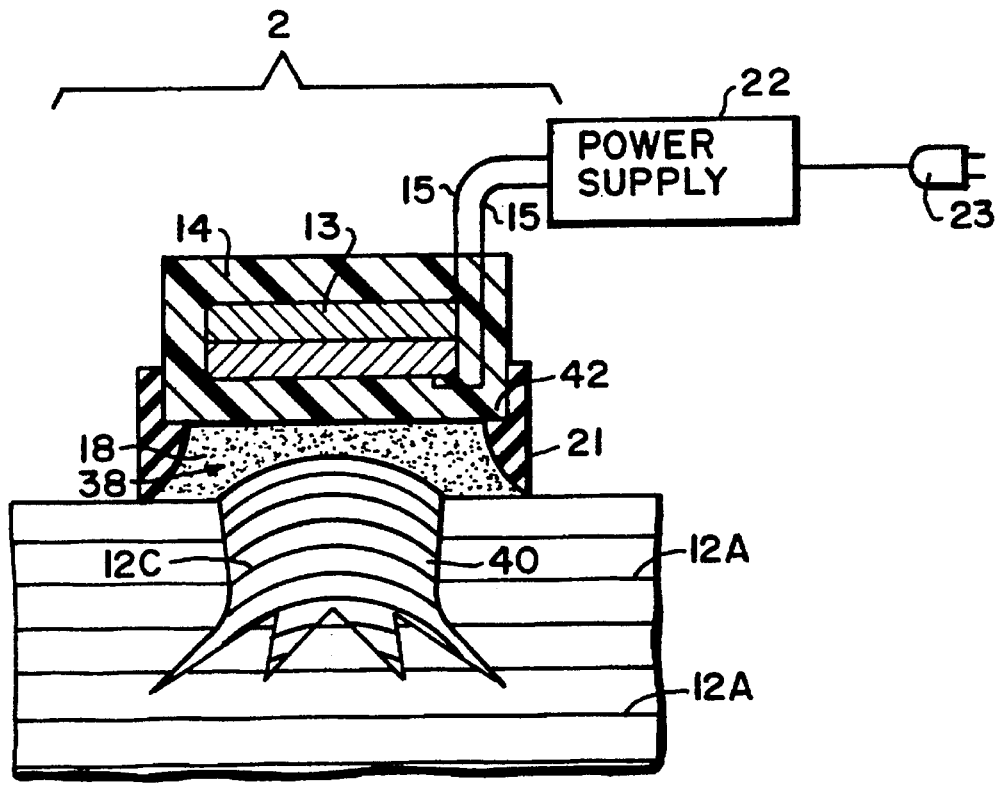
FIGS. 2A and 2B show cross-sectional views of the invention as it is used during an ultrasound medicated process to deliver a controlled dosage of medication or cosmetics to a controlled depth in the skin or into the blood supply.

FIG. 2A shows the invention as it is used to deliver a controlled dosage of medication or cosmetics to a controlled depth in the skin, or into the blood supply. The device 2 comprises a housing 14, a piezoelectric transducer 13, connecting wiring 15 that connects the transducer 13 to the external ultrasonic power supply 22. The external power supply draws its power either from a standard household current through a connector 23 or is operated from a battery within the power supply. The device 2 further comprises a flexible sleeve 21 formed of rubber or the like which is supported on the housing and has a shoulder 42 which in conjunction with the housing 14 forms a controlled volume chamber 38 to hold a predetermined amount of therapeutic agent 18 to be delivered into the diseased area of the skin, such as a wart 40. The device 2 is shown in position on top of the outer surface of the stratum corneum 11, with outermost skin layer consisting of flat, dead cells filled with keratin fibers surrounded by ordered lipid bilayers 12A. This ordered structure of the lipid bilayers normally provides an impermeable protection of the anatomy. Also shown under the irradiation area is a wart 40 having a keratinous structure 12C which cannot be penetrated by the drug molecules. These warts are typically pared by the physician in an attempt to provide access for topical therapeutic agents into the deeper structures of the wart. The therapeutic agent may be in liquid, paste or gel form and the like.

Figure 2B:
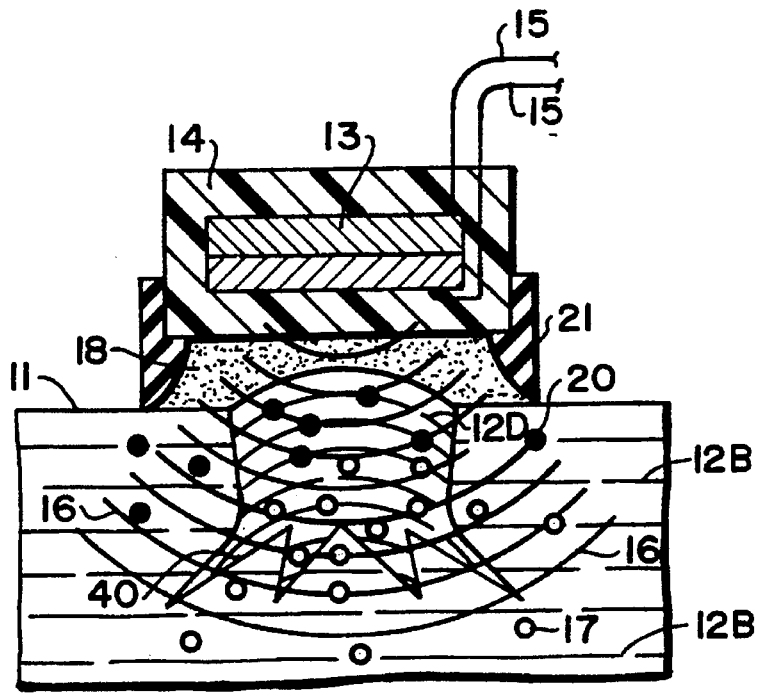

FIG. 2B shows the energized transducer 13 generating ultrasonic waves 16 in the frequency range of 15,000 to 25,000 Hertz, providing ultrasonic cavitation to develop, grow and oscillate microscopic air and/or vacuum pockets 17 which act to disorganize the lipid bilayers 12B depicted by dashed lines in this illustration. The vacuum pockets and the disorganization of the lipid bilayers temporarily eliminate the barrier properties of the skin, and provide penetrable channels for therapeutic compounds through the stratum corneum 11 into the deeper layers of the living skin, into the disordered internal structure 12D of the wart 40, and the underlying tissues. Finding the open channels through the disordered lipid bilayers 12B, the molecules 20 of the therapeutic compounds will penetrate through the stratum corneum 11 into the living skin, into the internal structure of the wart 40 and underlying tissues.

The effective dosage delivered from a particular volume of medication into the anatomy, at a given ultrasonic frequency and intensity, is directly proportional to the skin surface area irradiated by the ultrasonic transducer, the available volume of medication, and the exposure time. It is inversely proportional to the molecular weight of the drug to be delivered. To assure the accuracy of the effective dosage delivered into the skin, in addition to the exact irradiation time, the available amount of medication must also be the same each time the device is used. The function of the controlled volume chamber 38 is to assure that the amount of medication available is the same from application to application. The surface contact area of the chamber 38 is determined by the size of the transducer, while the thickness of the chamber is sized according to the molecular weight of the medication to be delivered into the skin.

Figure 2C:
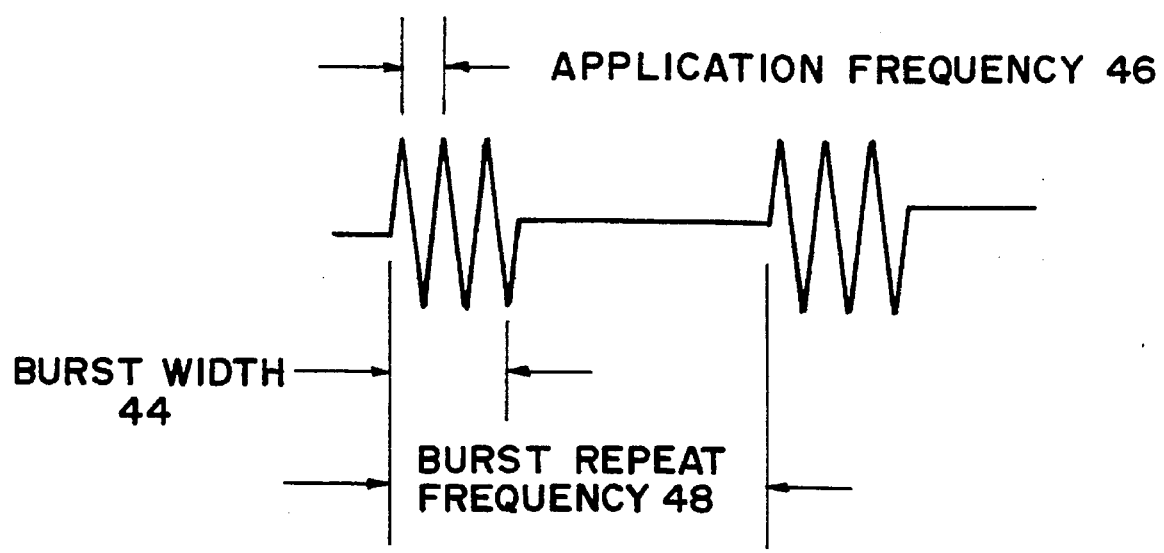
FIG. 2C is a waveform diagram illustrating the manner in which depth of penetration of a therapeutic agent may be controlled.

A method to control the penetration depth of the therapeutic agents is depicted in FIG. 2C. It was discovered that the depth of penetration of therapeutic agents for a particular application frequency 46 is proportional to the burst width 44 of this frequency. When a burst is terminated and the ultrasonic pressure waves are stopped, the molecules passing through the passageways will also stop. When the next burst is applied, it tends to introduce new molecules into the passage, finding channels which are still open rather than the channels which are partially blocked by the previously introduced molecules. Therefore, to limit the penetration depth of the therapeutic agents, very short, microseconds length bursts are applied. To deepen penetration, the burst width is increased, keeping the molecules introduced into the passageways moving. The dosage delivered is proportional to the sum of the ultrasonic energy applied. Therefore, to deliver a particular dosage into the top layer of the skin, a large number of very short bursts are applied. To deliver the same dosage deep into the skin and into the underlying tissues, a smaller number of bursts of longer duration are applied. Heat buildup in tissue is controlled by the duty cycle of the ultrasonic energy. The duty cycle is the ratio of the burst width 44, or the power on time, to the burst repeat frequency 48, the sum of the on and off times. To reduce heat buildup, the duty cycle of the equipment is lowered.

Figure 3A:
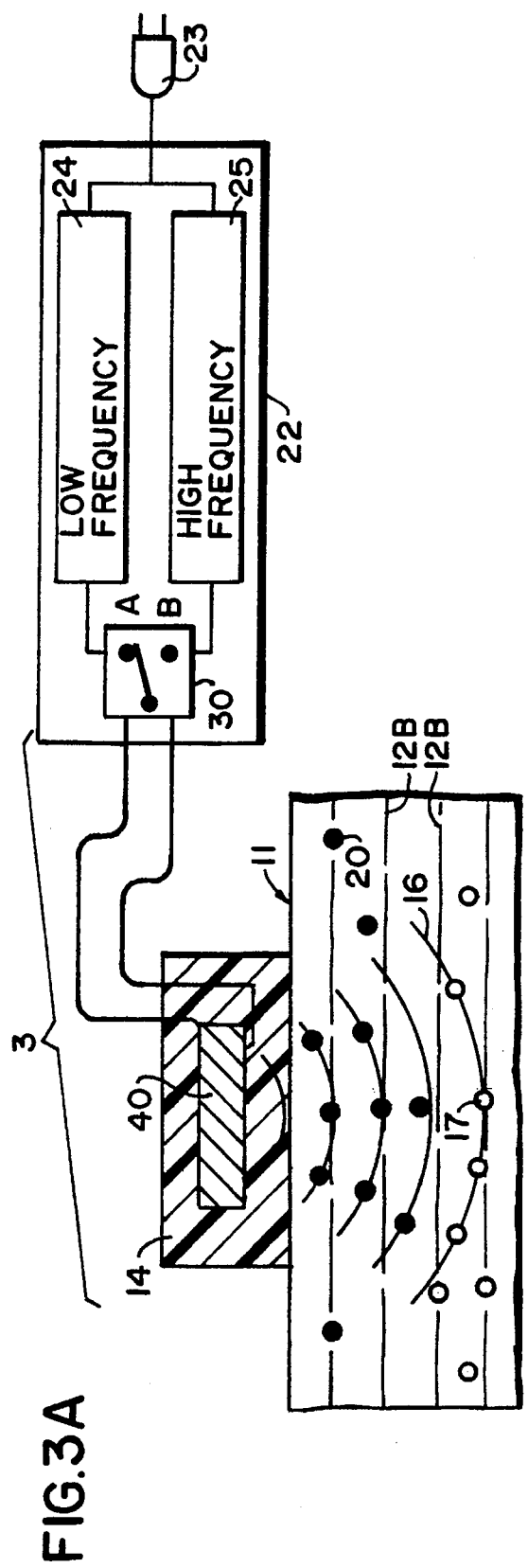
FIGS. 3A and 3B show an enhanced version of the invention and a sequence of operation that includes the low frequency passageway development, the delivery of medication into the skin utilizing ultrasonic pressure waves, followed by a high frequency sealing operation to quickly reestablish the environmental protection capabilities of the skin.
Figure 3B:
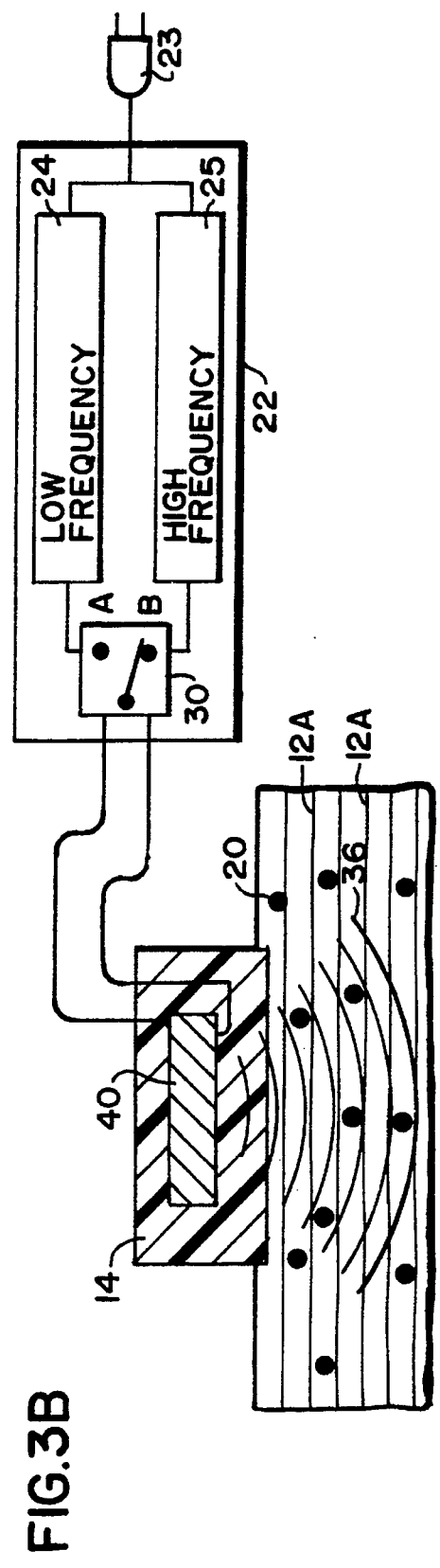

FIGS. 3A and 3B show an enhanced version of the invention and a sequence of operation that includes a low frequency passageway development, the delivery of medication into the skin utilizing ultrasonic pressure waves, followed by a high frequency sealing operation to quickly reestablish the environmental protection capabilities of the skin.

An ultrasonic drug delivery device 3 is shown in FIG. 3A. The drug delivery device 3 comprises a piezoelectric transducer 40, connecting wiring 15 that connects the transducer 40 to the external ultrasonic power supply 22. The thickness and the material of the piezoelectric transducer 40 is designed to operate at two frequencies. At the megahertz frequency range, the transducer 40 operates at its natural resonant frequency. At the kilohertz range, the transducer 40 operates at one of the subharmonic frequencies of its natural resonant frequency. The external power supply 22 draws its power either from a standard household current through a connector 23 or is operated from a battery within the power supply. The power supply 22 comprises two ultrasonic generators. The low frequency generator 24 operates in the kilohertz range while the high frequency generator 25 operates in the megahertz range. The low frequency generator 24 operates in the frequency range of 15,000 to 25,000 Hertz. It is connected to the transducer 40 through two position selector switch 30, shown in position A. The transducer 40 so energized generates ultrasonic waves 16 at the frequency of the power supply 24 producing cavitation in the skin, to develop, grow and oscillate microscopic air and vacuum pockets 17 which act to disorder the lipid bilayers 12B depicted by dashed lines in this illustration. The vacuum pockets and the disordered lipid bilayers 12B temporarily eliminate the barrier properties of the skin, and provide penetrable channels for medical and cosmetic therapeutic agents through the epidermis into the deeper layers of the living skin and the underlying tissues. The ultrasonic pressure waves 16 also act as mechanical forces to drive the molecules 20 of the therapeutic agents into the passageways through the stratum corneum into the deeper living sections of the skin.

Upon delivery of the therapeutic dosage of the medication into the skin, it is desirable to quickly restore the low permeability sealing properties of the skin. The body's natural function will reorganize the lipid bilayers into an ordered form again upon the termination of the cavitational ultrasonic pressure waves 16, however, this process is relatively slow. The reordering of the lipid bilayers can be accelerated by the application of megahertz frequency low intensity noncavitating ultrasonic waves, producing gentle angstrom wavelength vibrations in the stratum corneum.

FIG. 3B shows the invention in the high frequency mode of operation. The megahertz frequency generator 25 is connected to the transducer 40 through position B of the two position switch 30. The megahertz frequency range ultrasonic waves 36 generates angstrom wavelength vibrations in the keratin fibers and the surrounding lipid bilayers to augment the body's natural function to reestablish the order of the lipid bilayers 12A in the stratum corneum, and to effectively seal the body against further penetration of both desired and undesired invading molecules. The kilohertz and megahertz frequency range ultrasonic vibrations can be generated by two or more independent transducers, if desired.

While the preceding description contains may specificities, these should not be construed as limitations on the scope of the invention, but rather as an exemplification of a preferred and additional embodiments thereof. Many other variations are possible. Skilled artisans will readily be able to change dimensions, shapes and construction materials of the various components described in the embodiments and adopt the invention to all types of sonic energy applications, from the low frequency sonic to the high frequency ultrasonic range. Accordingly, the scope of the invention should be determined not by the embodiments illustrated, but by the appended claims and their legal equivalents.

What is claimed:

1. The method of facilitating the penetration of a therapeutic agent through a person's skin comprising, applying relatively low frequency ultrasonic pressure waves in a range of about 15000 to about 25000 Hz to the skin of sufficiently high intensity to cause cavitation in the skin thereby opening up passageways through the stratum corneum by disordering the lipid bilayers and increasing the permeability of the skin to allow the penetration of a therapeutic agent for a limited time period, terminating the application of low frequency ultrasonic pressure waves to the skin, then promptly applying a therapeutic agent to the skin before the natural function of the person's body decreases the permeability of the skin and restores the normal environmental protection of the body; and subsequently applying gentle high frequency noncavitating ultrasonic vibrations to the keratin fibers and the surrounding lipid bilayers of the stratum corneum to augment the body's natural function to reestablish the order of the lipid bilayers and to effectively seal the body against further penetration of invading molecules.

2. The method as defined in claim 1 wherein the ultrasonic pressure waves are applied in a pulsed modality to reduce the tissue heating effects of said ultrasonic pressure waves.

3. The method as defined in claim 1 wherein said ultrasonic pressure waves are produced by applying electrical signals of a particular frequency to a piezoelectric transducer, and including the step of varying the burst width of said frequency to control the depth of penetration of the therapeutic agent.

4. The method as defined in claim 3 wherein said burst width is decreased to reduce the depth of penetration and is increased to increase the depth of penetration.

5. The method as defined in claim 1 further comprising a step of varying the burst width of the low frequency pressure wave, said burst width being proportional to the depth of penetration of the therapeutic agent so that said burst width is decreased to reduce the depth of penetration and increased to increase the depth of penetration.

6. The method of facilitating the penetration of a therapeutic agent through a person's skin comprising, applying a therapeutic agent to the skin, then applying through the therapeutic agent relatively low frequency ultrasonic pressure waves to the skin of sufficiently high intensity to force said therapeutic agent into the skin and concurrently cause cavitation in the skin thereby opening up passageways through the stratum corneum by disordering the lipid bilayers and increasing the permeability of the skin to allow the penetration of the therapeutic agent, subsequently terminating the application of low frequency ultrasonic pressure waves to the skin, and applying relatively high frequency noncavitating ultrasonic vibrations into the keratin fibers and the surrounding lipid bilayers of the stratum corneum to augment the body's natural function to reestablish the order of the lipid bilayers and to effectively seal the body against further penetration of invading molecules.

7. The method as defined in claim 6 including the step of providing a predetermined controlled amount of the therapeutic agent prior to application thereof to the skin.

8. The method as defined in claim 6 wherein said ultrasonic pressure waves are produced by applying electrical signals of a particular frequency to a piezoelectric transducer, and including the step of varying the burst width of said frequency to control the depth of penetration of the therapeutic agent.

9. The method as defined in claim 8 wherein said burst width is decreased to reduce the depth of penetration and is increased to increase the depth of penetration.

10. The method as defined in claim 6 further comprising a step of varying the burst width of the low frequency pressure wave, said burst width being proportional to the depth of penetration of the therapeutic agent so that said burst width is decreased to reduce the depth of penetration and increased to increase the depth of penetration.

11. Apparatus for facilitating the penetration of a therapeutic agent through a person's skin and driving said agent into the skin comprising, a housing, said housing supporting a piezoelectric transducer including at least one active element for contracting and expanding volumetrically when energized in response to a changing electrical field and generating vibrations of ultrasonic energy, an ultrasonic power supply to generate ultrasonic frequency electric signals, means coupling said power supply to said piezoelectric transducer, and a sleeve coupled to the housing having an open end and defining a measuring chamber of a predetermined control volume for supporting a predetermined controlled amount of therapeutic agent therein in contact with the skin to couple the ultrasonic vibrations through said therapeutic agent to the skin whereby an accurately controlled amount of said therapeutic agent is driven into the skin wherein said open end of said sleeve has a flexible marginal edge for forming a seal for the chamber with the skin and wherein said ultrasonic vibrations pass through the open end during operation.

* * * * *